(12) United States Patent
Hyatt

(10) Patent No.: US 6,262,279 B1
(45) Date of Patent: Jul. 17, 2001

(54) PREPARATION OF TOCOPHEROLS

(75) Inventor: John Anthony Hyatt, Kingsport, TN (US)

(73) Assignee: Eastman Chemical Co., Kingsport, TN (US)

( * ) Notice: Subject to any disclaimer, the term of this patent is extended or adjusted under 35 U.S.C. 154(b) by 0 days.

(21) Appl. No.: 09/348,192

(22) Filed: Jul. 6, 1999

Related U.S. Application Data

(60) Provisional application No. 60/091,868, filed on Jul. 6, 1998.

(51) Int. Cl.$^7$ ................................................. C07D 311/74
(52) U.S. Cl. ........................................... 549/408; 549/412
(58) Field of Search ...................................... 549/408, 412

(56) References Cited

U.S. PATENT DOCUMENTS

| 4,305,876 | 12/1981 | Barner et al. . |
| 5,591,772 | 1/1997 | Lane et al. . |
| 5,849,755 | 12/1998 | Englert et al. . |

FOREIGN PATENT DOCUMENTS

| 0 283 946 | 9/1988 | (EP) . |

OTHER PUBLICATIONS

H.J. Kabbe, H. Heitzer, "Eine neue Synthese von 3,4–Dehydro–α–tocotrienol und Vitamin E", Synthesis, 888 (1978).

B.C. Pearce et.al. "Inhibitors of Cholesterol Biosynthesis. 2. Hyopcholesterolemic and Antioxidant Activities of Benzopyran and Tetrahydronapthalene Analogs of the Tocotrienols" J.Med Chem. 37, 526 (1994).

S. Kasparek "Chemistry of Tocopherols and Tocotrienols" Chapter 2 pp. 8–65. L. Machlin, ed., "Vitamin E: A Comprehensive Treatise", Marcel Dekker, NY, 1980.

A. Jacob, M. Steiger, A.R Todd and T.W. Work (J. Chem. Soc. 542, 1939).

T.W. Green "Protective Groups in Organic Synthesis" pp. 10–86, John Wiley and Sons, 1981.

Primary Examiner—Joseph K. McKane
Assistant Examiner—Taofiq A Solola
(74) Attorney, Agent, or Firm—Matthew W. Smith; Bernard J. Graves, Jr.

(57) ABSTRACT

The invention provides methods for producing tocopherol compounds of the Vitamin E family by reduction of various 4-chromanone trienol materials. In preferred embodiments the invention provides methods of preparing and hydrogenating 4-chromanone trienols to provide gamma-tocopherol.

26 Claims, No Drawings

PREPARATION OF TOCOPHEROLS

CROSS REFERENCE TO RELATED APPLICATIONS

This application claims priority to U.S. Provisional Application Ser. No. 60/091,868, entitled "Method of Vitamin Production", filed Jul. 6, 1998.

FIELD OF THE INVENTION

This invention relates generally processes for producing vitamin E and related compounds. In particular, the invention relates to processes for producing tocopherols and certain tocopherol derivatives, including gamma

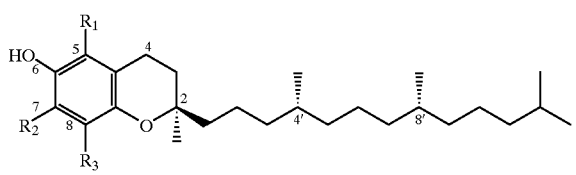

1=d-tocopherols
   1a=d-alpha tocopherol $R_1=R_2=R_3=CH_3$
   1b=d-beta tocopherol $R_1=R_3=CH_3$, $R_2=H$
   1c=d-gamma tocopherol $R_1=H$, $R_2=R_3=CH_3$
   1d=d-delta tocopherol $R_1=R_2=H$, $R_3=CH_3$ tocopherol.

BACKGROUND OF THE INVENTION

The naturally occurring vitamin E family of compounds includes a number of homologous tocopherols 1, and tocotrienols 2.

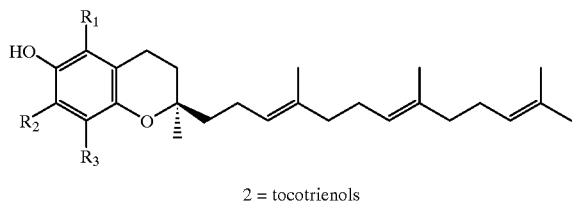

2 = tocotrienols

These compounds differ in the number and position of aromatic ring methyl groups, and in the degree of side chain unsaturation.

Naturally occurring vitamin E (d-alpha-tocopherol, 1a) is an important nutritional supplement in humans and animals, and is obtained commercially by isolation from a variety of plant oils, or semi-synthetically by ring methylation of less-substituted tocopherol compounds, such as the related naturally occurring d-gamma-tocopherol 1b. An important source of tocopherols is chemical synthesis, which provides d,l-alpha-tocopherol, 3. Commercially available samples of 3 are typically composed of mixtures of optical isomers at the 2, 4', and 8' positions,

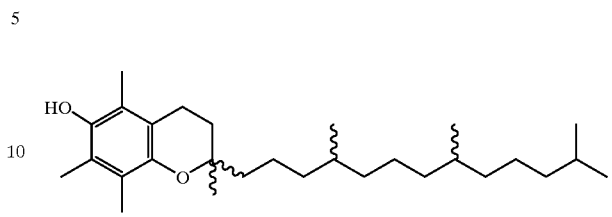

3 = d, l-alpha tocopherol

D,L-gamma tocopherol, 4, differs from 3 only by the presence or absence of a 5-methyl substituent on the aromatic ring.

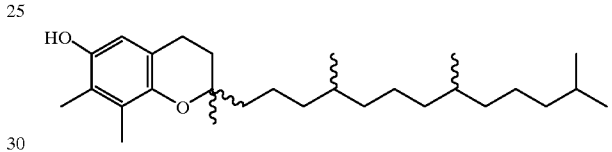

4 = d, l-gamma tocopherol 3 and 4 provide much of the biological activity of 1a, and are widely used due to lower cost and greater availability. The other tocopherols have also been shown to possess important antioxidant or vitamin E activity in mammals and humans, and are included in many modern commercial nutritional supplements. For a general discussion of vitamin E chemistry, see L. Machlin, ed., "Vitamin E: A Comprehensive Treatise", Marcel Dekker, NY, 1980.

It is known that d,l-alpha-tocopherol 3 is obtained by reacting trimethylhydroquinone with either phytol or isophytol in the presence of an acid. Other known technologies for preparation of tocopherols and tocotrienols were reviewed by S. Kasparek in chapter 2 of Machlin's Treatise, pp. 8–65. References 140–166 of Kasparek's chapter provide the primary references to other methods of preparing compound 3.

Kabbe and Heitzer reported a multi-step synthesis of d,l-alpha-tocopherol, 3, (Synthesis 888, 1978). Two known compounds, (2-acetyl-3,5,6-trimethylhydroquinone and farnesylacetone 5) were condensed to give a 4-chromanone tocotrienol compound 6, whose structure is shown in Scheme 1 below.

Scheme 1

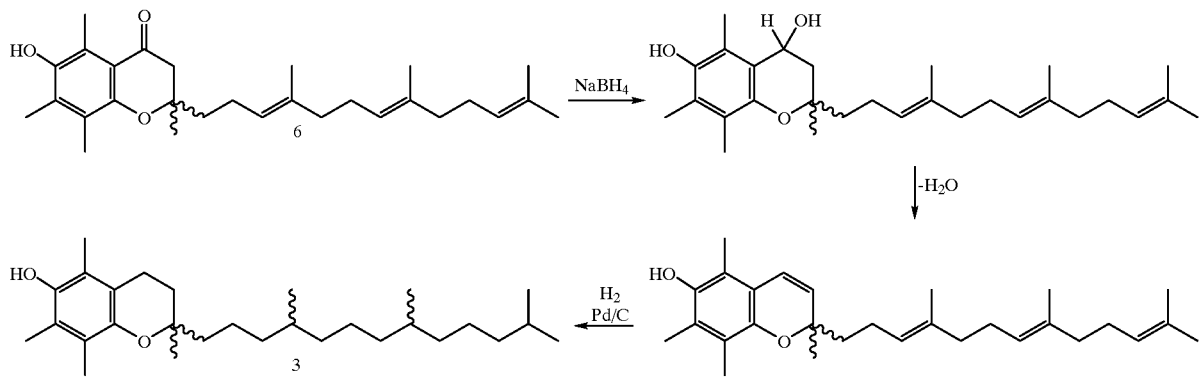

The 4-keto group of compound 6 was (a) reduced with sodium borohydride to give the corresponding alcohol, (b) the alcohol was dehydrated to give the tetra-olefin, and (c) the four carbon-carbon double bonds of the tetra-olefin were hydrogenated to give d,l-alpha-tocopherol 3. Kabbe et.al.'s multi-step process to produce alpha tocopherol from a 4-chromanone trienol is industrially undesirable however, because stoichiometric quantities of expensive borohydride reagents are consumed and undesirable borate wastes are formed, multiple reaction steps and solvents are employed, and equipment and operational costs are high. Kabbe et.al. made no suggestion that a simpler process could be employed.

The multi-step sequence is apparently necessary, at least in the case of preparation of alpha-tocopherol. The current inventors have found that the tri-methyl-4-chromanone compound 6, is not detectably converted to alpha-tocopherol by direct catalytic hydrogenation. Attempts to carry out direct hydrogenation of compound 6, (as illustrated in Scheme 2 and described in Comparative Example 1) have led instead to formation of a saturated ketone, 7. No further hydrogenation of 7 occurs, and no detectible quantity of 3 is produced.

Scheme 2

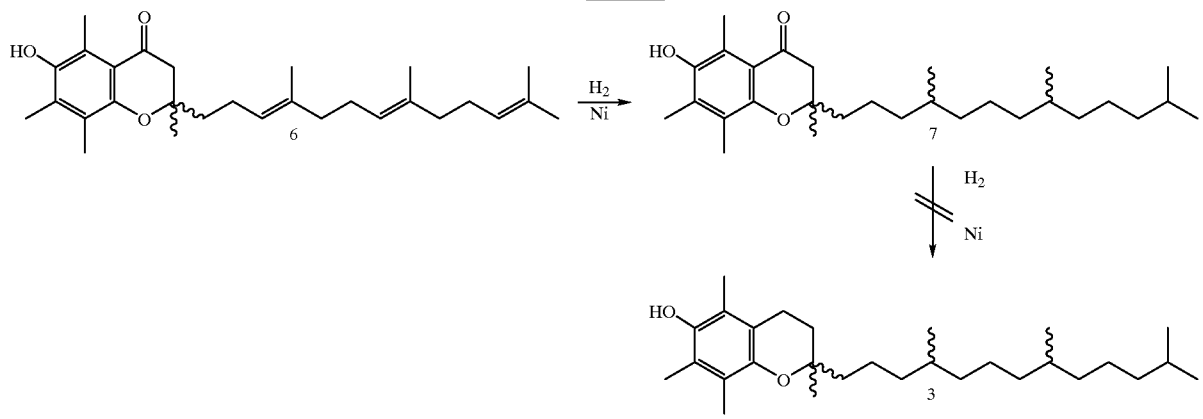

In the "gamma" series of compounds (i.e. 7,8-dimethyl tocopherols and tocotrienols), gamma tocopherol, 4, was first chemically synthesized by Jacob, Steiger, Todd and Wilcox (*J. Chem. Soc.* 1939, 542) by reacting the monobenzoate ester of 2,3-dimethylhydroquinone with phytyl bromide in the presence of zinc chloride, followed by removal of the benzoate to give a low yield (22%) of gamma-tocopherol. More recently, U.S. Pat. No. 5,591,772 to Lane, Qureshi, and Salser reported isolation of the 7,8-dimethyl-4-chromanone trienol compound 8 (whose structure is shown in Scheme 3) from natural sources.

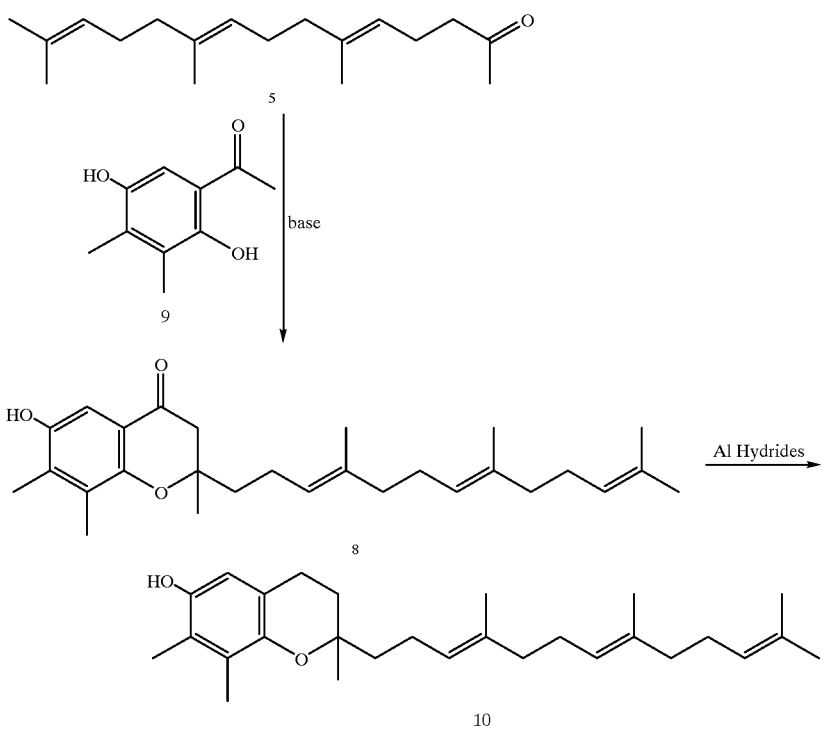

Pearce et al. (*J. Med. Chem.* 37, 526–541, 1994) adapted the method of Kabbe and Heitzer to synthesize compound 8 in racemic form and partially reduce it. See Scheme 3. 2-Acetyl-5,6-dimethyl-hydroquinone, 9, and farnesylacetone, 5, were condensed to give compound 8, then the 4-keto group of 8 was chemically reduced and removed with stoichiometric quantities of aluminum hydride reagents, to give the gamma-tocotrienol derivative 10. Lane et. al. and Pearce et.al. did not suggest a process for converting the 4-chromanone compound 8 to gamma tocopherol 4. Conversion of compound 8 to compound 10 with aluminum hydrides, then to gamma-tocopherol, compound 4, would require additional reduction steps and have many of the disadvantages of Kabbe's process for the production of alpha-tocopherol.

Thus, despite the various known methods for preparing or isolating compounds related to the vitamin E family of compounds, there remains a need for simpler and more efficient methods of production of tocopherol derivatives.

SUMMARY OF THE INVENTION

In accordance with the purpose(s) of this invention, as embodied and broadly described herein, this invention, in one aspect, relates to a process for preparing a tocopherol compound, comprising reducing a 4-chromanone trienol material

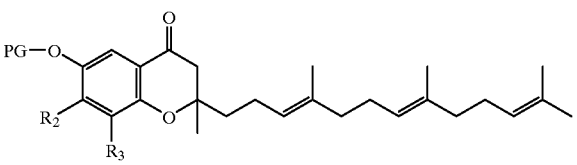

in the presence of at least one hydrogen donor and a catalyst, under conditions and for a time sufficient to form at least some of a tocopherol compound

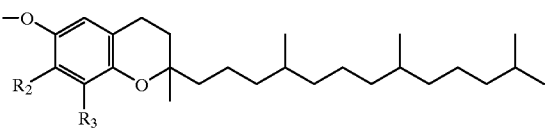

wherein $R_2$ and $R_3$ are methyl or hydrogen, and PG is hydrogen or a removable protecting group.

The invention further provides a process for preparing gamma-tocopherol by hydrogenation, comprising reacting

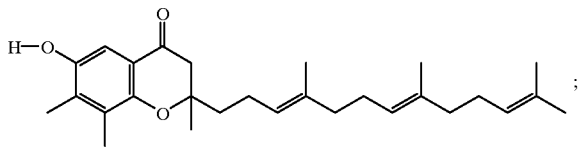

and H$_2$ at a pressure from about 400 to about 750 psig; in a reactor containing a solvent and a Raney nickel catalyst, at a temperature from about 135° C. to about 200° C., for a time from about 1 to about 10 hours.

In view of Kabbe et.al.'s failure to suggest direct hydrogenation of the 4-chromanone compound 6 to produce alpha-tocopherol, and the failure of attempts by the current inventors to produce alpha-tocopherol by direct hydrogenation of 6, it is particularly unexpected and surprising that gamma tocopherol, which differs from alpha-tocopherol only by the absence of a methyl group at the 5-position of the aromatic ring, can be produced in very high yield by the instant methods.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE PREFERRED EMBODIMENTS

The present invention may be understood more readily by reference to the following detailed description of preferred embodiments of the invention and the examples included therein.

Definitions and Use of Terms

Before the present compounds, compositions and methods are disclosed and described, it is to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

A protecting group (PG) is defined for the purposes of this invention as a substituent group which can be chemically bound to a phenolic oxygen atom, and subsequently removed (either chemically, in-vitro, or in-vivo) from the phenolic oxygen atom by predictable methods. Examples of many of the possible protective groups can be found in *Protective Groups in Organic Synthesis* by T. W. Green, John Wiley and Sons, 1981, pp. 10–86, which is incorporated herein by reference in its entirety.

A reducing agent is defined for the purposes of this invention as any device, chemical compound, or composition which is capable of donating or transferring one or more electrons to another chemical compound or composition. A reducing agent may or may not also donate hydrogen nucleii to the other chemical composition.

A hydrogen donor is defined for the purposes of this invention as a chemical compound or composition which is capable of donating or transferring a hydrogen nucleus to a chemical compound or composition which is being reduced. A hydrogen donor may or may not also donate electrons to the chemical compound or composition. The hydrogen donors may donate or transfer the hydrogen nuclei to another chemical compound or composition in association with various numbers of electrons (including acidic hydrogen, H$^+$, with no associated electrons; neutral hydrogen, as H·, H-Donor, or H$_2$, wherein the donor provides approximately one associated electron per hydrogen nucleus; or as hydridic hydrogen, H$^-$, having approximately two associated electrons per hydrogen nucleus).

The terms "alkene" or "olefin" as used herein intends a carbon-containing compound or functional group of 2 to 24 carbon atoms having 1 to 4 carbon-carbon double bonds, excluding any carbon-carbon double bonds which are part of an aromatic ring. Preferred alkene or olefing groups within this class contain 2 to 12 carbon atoms. Asymmetric structures such as (AB)C=C(CD) are intended to include both the E and Z isomers. This may be presumed in structural formulae herein wherein an asymmetric alkene is present, or it may be explicitly indicated by the bond symbol ⚌.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a phenolic residue in a compound refers to one or more aryl groups having an oxygen singly bonded to a carbon atom which is part of an aryl ring, regardless of whether the residue is obtained by reacting phenol or an ester thereof to obtain the compound.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

Discussion

The present invention provides a process for preparing a tocopherol compound, comprising reducing a 4-chromanone trienol material

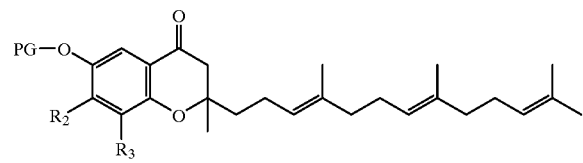

in the presence of at least one hydrogen donor and a catalyst, under conditions and for a time sufficient to form at least some of a tocopherol compound

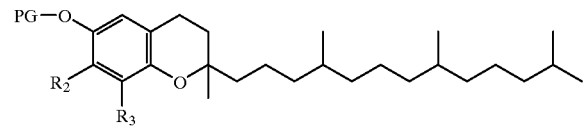

wherein $R_2$ and $R_3$ are methyl or hydrogen, and PG is hydrogen or a protecting group. The tocopherol compound may have any combination of optical isomers at the 2, 4', and 8' carbon atoms.

In one preferred embodiment, the protecting group and the oxygen bonded to the protecting group forms a $C_2-C_{25}$ ester group. In these embodiments, the protecting group comprises the acyl portion of a carboxylic acid. The acyl portion of the carboxylic acid may be derived from a $C_2-C_{25}$ carboxylic acid, or preferably a $C_2-C_{12}$ carboxylic acid. Examples of the ester groups which can be formed include but are not limited to an acetic acid ester group, a propionic acid ester group, a succinic acid ester group, benzoic acid ester groups, fatty acid ester groups, esters of amino acids, and the like.

In certain preferred embodiments the 4-chromanone trienol material comprises

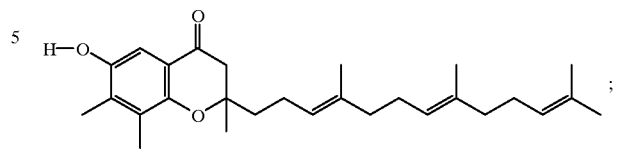

and the tocopherol compound comprises

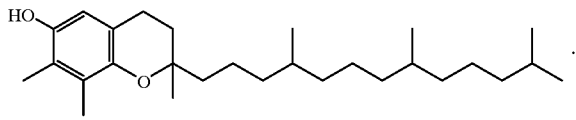

In the above processes of the invention, the 4-chromanone trienol materials are reduced in the presence of at least one hydrogen donor and at least one catalyst. In particular, the three carbon-carbon double bonds and the carbon-oxygen double bond of the 4-chromanone trienol material are reduced. The carbon-carbon double bonds and the carbon-oxygen double bond may be reduced in any sequence or order. The reduction steps may be preceded by substitution of the starting material to form chemical intermediates with a variety of heteroatomic substituent groups. Chemical intermediates having various substituents bonded to the 4-chromanone trienol carbon skeleton (either transitory and stable) may be involved during the process of reducing. Preferably, all the carbon-carbon and carbon-oxygen double bonds are concurrently reduced via a single reducing method.

At some point during the process of reducing, the carbon atoms having double bonds to be reduced are provided with new carbon-hydrogen bonds. Therefore, the reducing process requires at least one hydrogen donor, to provide the required hydrogen nucleii. During the process of reducing, a source of electrons must also be supplied by a reducing agent. The hydrogen donor may or may not also function as the reducing agent, to supply the required electrons. In many embodiments, the hydrogen donor does supplies electrons for the reduction step, and functions as a reducing agent. If the hydrogen donor does not supply electrons for the reduction step, a separate reducing agent must be provided to supply electrons for the reducing step. A plurality of reducing agents, or hydrogen donors, or mixtures of reducing agents and hydrogen donors can be utilized. More preferably, the reducing occurs in the presence a single hydrogen donor, which also supplies electrons, and therefore no separate reducing agent is required.

In another preferred embodiment of the process, the reducing is by hydrogenation. Hydrogenation is defined for the purposes of this invention as a process of reducing in which a double bond is replaced by two carbon hydrogen bonds, wherein the hydrogen atoms (having both hydrogen nucleii and electrons) are transferred from the catalyst to a carbon atom.

The hydrogen donor for hydrogenation reactions need not comprise $H_2$. In fact, it is known in the art that carbon-carbon double bonds, and carbon-oxygen double bonds can be reduced via "transfer hydrogenation" reactions. Transfer hydrogenations do not employ $H_2$ as a hydrogen donor. A variety of hydrogen donors for transfer hydrogenation reactions are known, which include but are not limited to hydrazine, alcohols, and silanes.

The most preferred hydrogen donor is $H_2$, i.e. hydrogen gas. The $H_2$ can be present at a pressure from about atmospheric pressure to about 3000 psig. Preferably, $H_2$ is present at a pressure from 100 psig to about 1000 psig. Most preferably, $H_2$ is present at a pressure from about 400 psig to about 750 psig.

In the instant invention, the reduction of a 4-chromanone trienol material occurs in the presence of at least one catalyst. Catalysts are compounds or compositions which accelerate or improve the rate or selectivity of chemical reactions without substantial consumption of the catalyst compound or composition.

In one group of embodiments, the catalyst comprises Raney nickel, Raney cobalt, copper chromite, or a mixture thereof. In a particularly preferred embodiment, the catalyst comprises Raney nickel. As is well known in the art, each of these types of catalysts may or may not contain small quantities of modifier or promoter materials, such as another transition metal, sulfur or halide compounds. Raney nickel catalysts are particularly preferred catalysts for hydrogenation reactions employing $H_2$ as a hydrogen donor.

In alternative embodiments, the catalyst of the process comprises at least one transition metal, transition metal salt, transition metal complex, or a mixture thereof In these embodiments, the transition metal, transition metal salt, or transition metal complex may comprise chromium, molybdenum, tungsten, manganese, rhenium, iron, ruthenium, osmium, cobalt, rhodium, iridium, nickel, palladium, platinum, or copper. In preferred embodiments, the transition metal, transition metal salt, or transition metal complex may comprise nickel, palladium, platinum, ruthenium, rhodium, rhenium, or chromium.

Preferred transition metal salts comprise positively charged transition metal ions having chlorides, fluorides, bromides, iodides, nitrates, phosphates, sulfates, carboxylates, acetylacetonates, hydroxides, and the like as negatively charged counter-ions.

Typically, the transition metal components of the catalysts of the process are present in a quantity of from about 0.000001 to about 10 mole %, based on the moles of 4-chromanone trienol material, or more preferably from about 0.5 mole % to about 1.0 mole %.

In a preferred group of embodiments, the transition metal, transition metal salt, or transition metal complex comprising the catalyst is dispersed on or bonded to at least one support material. A wide variety of support materials are known as suitable in the art, and include but are not limited to support materials comprising carbon, activated charcoal, silica, alumina, titania, zirconia, a zeolite, a polymer, barium sulfate, or calcium sulfate. When the support material is a polymer, it is preferably an organic polymer or resin having functional groups suitable for bonding to the transition metal salt or complex.

In the embodiments comprising supported catalysts, the transition metal, transition metal salt, or transition metal complex comprises from about 0.1 to about 10 weight percent, based on the weight of the support material.

The instant process for reducing a 4-chromanone trienol material can be carried out in the absence of solvent. Alternatively the process can be conducted in the presence of at least one solvent, or a mixture of solvents. A wide variety of solvents suitable for reduction reactions are known in the art, and include but are not limited to water, $C_1$–$C_{12}$ alcohols, $C_2$–$C_{20}$ ethers, $C_1$–$C_{12}$ esters, or alkyl or aryl $C_5$–$C_{25}$ compounds containing only carbon and hydrogen. Preferred solvent species include, but are not limited to methanol, ethanol, n-propanol, isopropanol, butanol, ethyl acetate, ethylene glycol and ethylene glycol ethers, propylene glycol and propylene glycol ethers, and the like.

The reduction of a 4-chromanone trienol is carried out under conditions and for a time sufficient to form at least some of a tocopherol compound. Suitable conditions and reaction times can vary widely depending on the nature of the 4-chromanone trienol material, the type of reduction reaction and the quantity of the hydrogen donor, the catalyst, the reactor design, and a variety of other factors, as will be apparent to those of skill in the art.

Reduction reactions employing highly reactive reducing agents, such as boranes, aluminum hydrides, or silanes may be carried out below ambient temperatures, including temperatures as low as –78° C., or as high as 250° C. When the reduction reaction comprises a hydrogenation, hydrogenation is typically conducted at a temperature from about 50° C. to about 250° C. Preferably, hydrogenations are conducted at a temperature from about 135° C. to about 200° C.

The process of the instant invention can be carried out in batch reactors, or continuous reactors. The catalyst can be dissolved in the reaction medium, present as a slurry in the reaction medium, present in a fluidized bed, or present in a fixed bed. Suitable reaction times vary widely depending on other parameters of the reduction reaction. Typically the reaction time is from about 0.5 to about 48 hours. In certain preferred embodiments, the reaction time is from about 1 to 10 hours.

In one embodiment, the process of the invention additionally comprises removal of the protecting group from a protected tocopherol derivative, to form a tocopherol having the structure

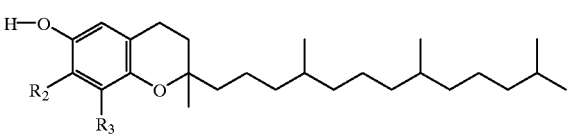

wherein $R_2$ and $R_3$ are hydrogen or methyl.

In certain embodiments of the the invention, the 4-chromanone trienol material is obtained by condensing farnesylacetone

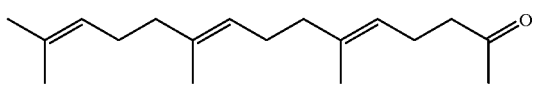

with a 2-acetyl-hydroquinone compound of the formula

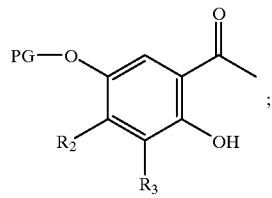

wherein $R_2$ and $R_3$ are methyl or hydrogen, and PG is hydrogen or a protecting group.

In other embodiment of the invention, the farnesylacetone is produced by a method comprising:
(a) reacting farnesol with a halogenating agent to provide a farnesyl halide compound;
(b) condensing the farnesyl halide compound with an acetoacetate ester, in the presence of a base, to provide a farnesyl acetoacetate ester; and
(b) hydrolyzing and decarboxylating the farnesyl acetoacetate ester; so as to produce farnesylacetone.

The farnesol starting material of this embodiment may be provided by traditional methods of organic chemistry known in the art; or the farnesol may be isolated from natural or microbial sources, which may be improved by the methods of modern biotechnology as disclosed in U.S. Provisional Application Ser. No. 60/091,686, entitled "Method of Vitamin Production", to which this application claims priority. A variety of halogenating agents are known in the art for converting alcohols to alkyl halides. $PBr_3$ is preferred halogenating agent for converting farnesol to farnesyl bromide, a preferred farnesyl halide compound. Condensation of acetoacetate esters with alkyl halides, and hydrolysis and decarboxylation of the resulting substituted acetoacetate esters is well known in the art. Methylacetoacetate and ethylacetoacetate are preferred acetoacetate esters for condensation with farnesyl halides.

In one highly preferred embodiment, the instant invention provides a process for preparing gamma-tocopherol by hydrogenation, comprising reacting

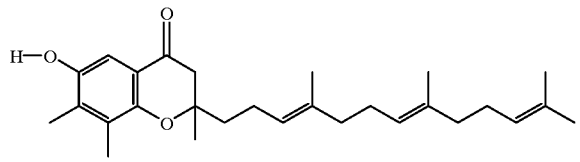

and $H_2$ at a pressure from about 400 to about 750 psig; in a reactor containing a solvent and a Raney nickel catalyst, at a temperature from about 135° C. to about 200° C., for a time from about 1 to about 10 hours. The starting compounds of the invention may be readily synthesized using alternative techniques generally known to synthetic organic chemists. Suitable experimental methods for making and derivatizing aromatic compounds are described, for example, in the references cited in the Background section herein above, the disclosures of which are hereby incorporated by reference for their general teachings and for their synthesis teachings. Methods for making specific and preferred compounds of the present invention are described in detail in Examples 1 and 2 below.

Experimental

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

EXAMPLE 1

This example illustrates the production of d,l-gamma-tocopherol.

A solution of 18.9 grams (0.0446 mole) of the 7,8-dimethyl-4-chromanone tocotrienol 8, in 200 ml of ethyl alcohol was mixed with 2 grams (ethanol-wet weight) of Raney nickel catalyst, and hydrogenated with agitation at 500 psi of $H_2$ and 150° C. for 7 hrs. The reaction was cooled, vented, the catalyst filtered off, and the filtrate stripped of solvent under vacuum to leave 18.9 grams of a light yellow viscous oily product. Analysis of the product by proton NMR, mass spectroscopy, and IR spectroscopy established that it was gamma-tocopherol; assay by quantitative gas chromatography disclosed a composition of 97.07 wt %gamma-tocopherol, 4, the remainder being ethanol. The yield was 98.9% of theory.

EXAMPLE 2

This example is a comparative example to illustrate that the procedure for preparing gamma-tocopherol of Example 1 does not work for preparing alpha-tocopherol.

A solution of 6.2 grams of 4-chromanone 6 in 200 ml of ethanol was mixed with 2 grams (wet wt.) of Raney nickel catalyst and hydrogenated at 150° C., 500 psig $H_2$, with agitation for 7 hours. Workup as described in Example 1 gave 6.1 grams of a yellow syrup which was shown by proton NMR analysis to have no peaks consistent with the presence of olefins. Proton resonances observed (quartet, j=12 hz, 2.66 ppm) were consistent with a methylene at position 3, alpha to carbonyl; IR analysis showed the presence of the carbonyl group (1663 $cm^{-1}$) and the mass spectrum showed m/e 444 (calc. for 11, 444). Gas chromatographic analysis did not detect the presence of any alpha-tocopherol in the crude product.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for preparing a tocopherol compound, comprising reducing a 4-chromanone trienol represented by the formula

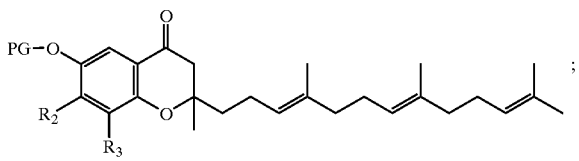

in the presence of at least one hydrogen donor and at least one transition metal containing catalyst, to form at least some of a tocopherol compound

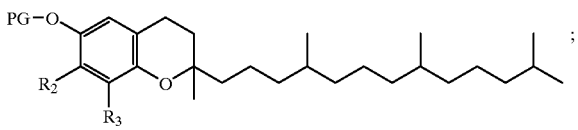

wherein $R_2$ and $R_3$ are methyl or hydrogen, and PG is hydrogen or a protecting group.

2. The process of claim 1, wherein the protecting group and the oxygen bonded to the protecting group form a $C_2$–$C_{25}$ ester group.

3. The process of claim 1, wherein the 4-chromanone trienol is

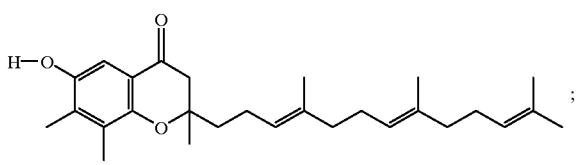

and the tocopherol compound is

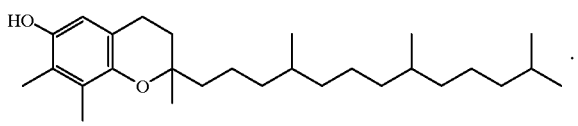

4. The process of claim 1, wherein the reducing occurs in the presence of a single hydrogen donor.

5. The process of claim 1, wherein the hydrogen donor is also a reducing agent.

6. The process of claim 1, wherein the reducing is by hydrogenation.

7. The process of claim 6, wherein the hydrogenation is a transfer hydrogenation.

8. The process of claim 4, wherein the hydrogen donor is $H_2$ at a pressure from about atmospheric pressure to about 3000 psig.

9. The process of claim 4, wherein hydrogen donor is $H_2$ at a pressure from 100 psig to about 1000 psig.

10. The process of claim 4, wherein the hydrogen donor is $H_2$ at a pressure from about 400 psig to about 750 psig.

11. The process of claim 1, wherein the catalyst is selected from the group consisting of Raney nickel, Raney cobalt, copper chromite, and a mixture thereof.

12. The process of claim 1, wherein the catalyst comprises Raney nickel.

13. The process of claim 1, wherein the catalyst is selected from the group consisting of at least one transition metal, transition metal salt, transition metal complex, and a mixture thereof; and wherein the transition metal, transition metal salt, or transition metal complex catalyst is selected from the group consisting of chromium, molybdenum, tungsten, manganese, rhenium, iron, ruthenium, osmium, cobalt, rhodium, iridium, nickel, palladium, platinum, and copper.

14. The process of claim 13, wherein the transition metal, transition metal salt, or transition metal complex catalyst is selected from the group consisting of nickel, palladium, platinum, ruthenium, rhodium, rhenium, and chromium.

15. The process of claim 13, wherein the transition metal, transition metal salt, or transition metal complex is present in a quantity of from about 0.000001 to about 10 mole %, based on the moles of 4-chromanone trienol compound.

16. The process of claim 13, wherein the transition metal, transition metal salt, or transition metal complex is dispersed on or bonded to at least one support material.

17. The process of claim 16, wherein the support material is selected from the group consisting of carbon, activated charcoal, silica, alumina, titania, zirconia, a zeolite, a polymer, barium sulfate, and calcium sulfate.

18. The process of claim 16, wherein the transition metal, transition metal salt, or transition metal complex is from about 0.1 to about 10 weight percent of the catalyst.

19. The process of claim 4, wherein the hydrogenation is conducted in the presence of at least one solvent.

20. The process of claim 19, wherein the solvent is selected from the group consisting of an alcohol, an ether, an ester, and a hydrocarbon.

21. The process of claim 19, wherein the solvent is selected from the group consisting of methanol, ethanol, n-propanol, isopropanol, ethyl acetate, and a mixture thereof.

22. The process of claim 6, wherein the hydrogenation is conducted at a temperature from about 50° C. to about 250° C.

23. The process of claim 6, wherein the hydrogenation is conducted at a temperature from about 135° C. to about 200° C.

24. The process of claim 6, wherein the reducing is carried out for a period of from about 0.5 to about 48 hours.

25. The process of claim 1, additionally comprising removal of the protecting group from the tocopherol compound, to form a tocopherol having the structure

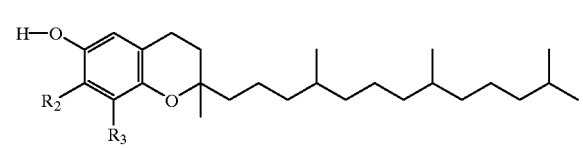

wherein $R_2$ and $R_3$ are hydrogen or methyl.

26. A process for preparing gamma-tocopherol by hydrogenation, comprising reacting
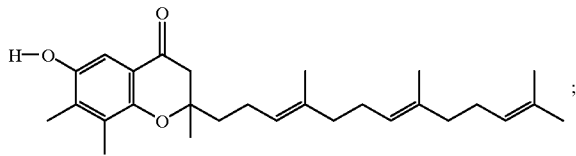
and $H_2$ at a pressure from about 400 to about 750 psig; in a reactor containing a solvent and a Raney nickel catalyst, at a temperature from about 135° C. to about 200° C., for a time from about 1 to about 10 hours.
* * * * *